(12) United States Patent
Hara et al.

(10) Patent No.: US 9,198,631 B2
(45) Date of Patent: Dec. 1, 2015

(54) X-RAY CT APPARATUS

(71) Applicant: Rigaku Corporation, Akishima, Tokyo (JP)

(72) Inventors: Yukihiro Hara, Hino (JP); Ayuta Yamada, Ome (JP); Kiyoshi Akiyama, Tachikawa (JP)

(73) Assignee: RIGAKU CORPORATION, Tokyo (JP)

( * ) Notice: Subject to any disclaimer, the term of this patent is extended or adjusted under 35 U.S.C. 154(b) by 302 days.

(21) Appl. No.: 13/834,870

(22) Filed: Mar. 15, 2013

(65) Prior Publication Data

US 2014/0064440 A1    Mar. 6, 2014

(30) Foreign Application Priority Data

Sep. 4, 2012   (JP) .................................. 2012-193825

(51) Int. Cl.
*A61B 6/00*   (2006.01)
*A61B 6/03*   (2006.01)

(52) U.S. Cl.
CPC .................. *A61B 6/508* (2013.01); *A61B 6/032* (2013.01); *A61B 6/035* (2013.01)

(58) Field of Classification Search
CPC ........ A61B 6/107; A61B 6/032; A61B 6/035; A61B 6/508; H05G 1/04; H01J 35/16
USPC .............................................. 378/203, 4–20
See application file for complete search history.

(56) References Cited

U.S. PATENT DOCUMENTS 5,937,028 A    8/1999   Tybinkowski et al.
7,072,434 B1 *  7/2006   Tybinkowski et al. ............ 378/4
7,151,817 B1   12/2006   Abraham et al.

FOREIGN PATENT DOCUMENTS

| JP | 11-347025     | 12/1999 |
| JP | 2001-520375 A | 10/2001 |
| JP | 2006-340963 A | 12/2006 |
| WO | 99/19715 A1   | 4/1999  |
| WO | WO 02/058100  | 7/2002  |

OTHER PUBLICATIONS

Search Report which is issued by the German Patent Office on Dec. 2, 2013, for the corresponding German Patent Application.

(Continued)

*Primary Examiner* — Courtney Thomas
(74) *Attorney, Agent, or Firm* — Mattingly & Malur, PC

(57) ABSTRACT

Small-sized X-ray CT apparatus obtaining a cross-section or 3D image of a sample, using X-rays. Included: an X-ray generating apparatus irradiating X-rays on the sample; an X-ray detecting device detecting X-rays passing through the sample; and a device processing a detection signal from the X-ray detecting device, to re-structure the cross-section or 3D image of the sample; an X-ray shielding member having an opening portion for introducing the sample therein on one end surface and being treated with an X-ray protection process on an entire periphery thereof; and a means rotationally driving the X-ray shielding member, wherein the X-ray generating apparatus and the X-ray detecting device are treated with the X-ray protection process, respectively, and are fixed on a wall surface of the X-ray shielding member at positions opposing to each other, putting an rotation axis thereof therebetween, and thereby constructed with the X-ray shielding member in one body.

13 Claims, 9 Drawing Sheets

(56) References Cited

OTHER PUBLICATIONS

Japanese Office Action received in corresponding Japanese Application No. 2012-193825 dated Jul. 28, 2015.

Hamanaka, I. et al., Micro X-ray CT Scanner for Animal Experiments—Introduction of a Recently Developed Product: "R_mCT2"-Proceedings of Okayama Association for Laboratory Animal Sciences, Apr. 2012, pp. 27-32.

* cited by examiner

X-RAY CT APPARATUS

BACKGROUND OF THE INVENTION

The present invention relates to an X-ray CT apparatus for obtaining a cross-section image or a 3D image of an inside of a sample to be inspected with using X-rays, and in particular, it relates to an X-ray shielding structure preferable for the CT apparatus, being relatively compact and light-weight, for use of small and middle-sized animals.

A CT (Computer Tomography) apparatus applying the X-rays therein is widely used, in particular, in a medical field, for obtaining the cross-section image or the 3D image of an inside of a sample to be inspected. Conventionally, the X-ray CT apparatus for use in the medical service is designed, in particular, for mainly enabling an inspection of a human body, and for that reason, it is large in the sizes and heavy in the weight, and further is high in the price thereof. Also, for the apparatus, because it brings the apparatus to be large in the sizes and heavy in the weight, it is difficult to shield the X-rays, as a whole thereof, and there is a necessity of installing the apparatus within an inspection room for the exclusive use thereof, which is surrounded by concrete walls and/or lead plates, etc., not penetrating the X-rays therethrough, for the purpose of preventing the X-rays from leaking outside and thereby exerting ill influences upon an operator, etc., and therefore, it is necessary for the operator to conduct an operation of the apparatus from another room, which is provided outside that inspection room.

On the other hand, in recent years, breeding a pet, such as, a dog or a cat (i.e., a pet boom), comes to be popular, widely, and an importance of the pet is also increased, as a member of a family, and accompanying with this, in relation to medical treatments or services for the pet, a demand of conducting a diagnosis and/or a treatment with using the X-ray CT apparatus comes to be strong.

Up to the present is only a way of introducing the CT for the human-use, unwillingly, for medical workers of the pet, being high in the price and large in the size, and also necessitating the inspection room for exclusive use thereof, being high in the price and large in the size, it is possible only, for a facility or institution restricted, to introduce that.

For dissolving such condition as mentioned above, in the following Patent Document 1 is proposed a relatively cheap-prices CT apparatus, being small-sized and easily movable, which does not necessitate the installation within the inspection room for exclusive use thereof.

PRIOR ART DOCUMENTS

Patent Documents

[Patent Document 1] Japanese Patent Laying-Open No. 2006-340963 (2006).

BRIEF SUMMARY OF THE INVENTION

However, the X-ray CT apparatus, according to the conventional art mentioned above, is characterized in that it has an X-ray shielding housing, for shielding the X-rays generating from an X-ray generator apparatus and scattering X-rays thereof, so as to not leak them outside. Thus, because of the structure of backing this housing, as a whole thereof, by a X-ray shielding material, such as, lead, etc., the apparatus results to be very heavy in the weight thereof, irrespective of the small-sizing thereof.

Also, on the other hand, for the operator, it is necessary to do the operation under the condition of inserting a part (for example, an arm) of her/his body in the shield housing, in particular, when doing, such as, positioning the sample to be inspected, etc.; there is a risk of exposure to radiation of the X-rays.

In more details thereof, in the embodiment described in the Patent Document 1 mentioned above is mentioned, "... being made the backing of lead plates 12a, 13a, 14a and 15a, upon a bottom wall 12 and each of cover members 13, 14 and 15, building up a housing, for supporting/receiving the X-ray generator apparatus 1 and the X-ray detector apparatus 2, it is possible to shield the X-rays generating from the X-ray generator apparatus 1, so as to prevent it from leaking into an outside of the housing 11. And, a door 16 is also backed by a lead plate 16a on the interior surface thereof, and a window 18 is made of a glass, including the lead therein, i.e., also having an X-ray shielding capacity. With this, it is possible to shield the X-rays, so that the X-ray CT apparatus 1 does not fall into such an apparatus that it needs determination of a management zone, in an outside thereof, as is defined by a first clause of an Article 3 of the regulation for prevention of ionizing radiation damage. Further, the door 16 may be made up with using the glass, including lead therein, so that an inside can be observed therefrom." (see column [0031])

Namely, with such conventional technology as mentioned above, for the purpose of obtaining an apparatus, not needing the determination of the management zone in the outside thereof, as is defined by the first clause of the Article 3 of the regulation for prevention of ionizing radiation damage, interior surfaces of a box-type (i.e., a cubic configuration) housing, as an entire thereof, being a housing surrounding the apparatus as a whole, are made up with members, each being backed by the lead plate. For that reason, the apparatus comes to be heavy-weighted, irrespective of the small-sizing thereof, and is limited in a place where that apparatus can be installed due to, such as, a problem of necessitating reinforcement of mechanical strength of a floor, etc., for example, and comes to be difficult in movement thereof because of the heavy weight.

Then, according to the present invention, being accomplished by taking such the problem(s) of the conventional art, as mentioned above, into the consideration thereof, in particular, relating to an X-ray shielding structure preferable for the X-ray CT apparatus, being small-sized and light-weighted, and an object thereof is to provide an X-ray CT apparatus having the structure for preventing the X-rays from leakage into an outside of the apparatus, with certainty, in addition to achieving the light-weight thereof, but without accompanying the large-sizing of the apparatus. Further, according to the present invention, it is also other object thereof, to provide an improved X-ray CT apparatus, being superior in the operability thereof, in addition to the object mentioned above.

For accomplishing the object mentioned above, according to the present invention, there is provided an X-ray CT apparatus, for obtaining a cross-section image or a 3D image of an inside of a sample, with using X-rays, comprising: an X-ray generating apparatus, which is configured to irradiate the X-rays on said sample; an X-ray detecting device, which is configured to detect the X-rays passing through said sample; and an apparatus, which is configured to process a detection signal from said X-ray detecting device and thereby to re-structure the cross-section image or the 3D image of the inside of said sample; and further comprising: an X-ray shielding member having an opening portion for introducing said sample therein on one end surface and being treated with an X-ray protection process on an entire periphery thereof; and a means for rotationally driving said X-ray shielding member, wherein said X-ray generating apparatus and said X-ray detecting device are treated with the X-ray protection process, respectively, and are fixed on a wall surface of said X-ray shielding member at positions opposing to each other, putting an rotation axis thereof therebetween, and thereby being constructed with said X-ray shielding member in one body.

Also, according to the present invention, in the X-ray CT apparatus, as described in the above, it is preferable that said X-ray shielding member is treated with the X-ray protection process, by backing a thin plate of a heavy metal or a heavy metal alloy, or is made of a thin plate of a heavy metal or a heavy metal alloy. Further, it is preferable that a sample setting portion is further attached on the opening portion of said X-ray shielding member, and further that said sample setting portion has an outer peripheral wall formed with an X-ray shielding member, a part thereof being constructed to be able to open/close, and further a top plate for moving the sample into an inside of said X-ray shielding member. In addition thereto, it is also preferable that a window portion for enabling to observe an inside is provided in a part of the outer peripheral wall formed with the X-ray shielding member for forming said sample setting portion, and further that an introduction opening is provided, further, in apart of the outer peripheral wall formed with the X-ray shielding member for forming said sample setting portion, and also is provided a member for preventing leakage of the X-rays from said introduction opening.

With the present invention mentioned above, it is possible to provide an X-ray CT apparatus, for enabling the small sizing/light weighting, as well as, for enabling to prevent leakage of X-rays outside the apparatus, with certainty, and further to provide an improved X-ray CT apparatus, being superior in the operability and/or the safety thereof, and thereby achieving an extremely superior effect, i.e., widening a field of the utility of the X-ray CT apparatus, largely.

BRIEF DESCRIPTION OF THE SEVERAL VIEWS OF THE DRAWING

Those and other objects, features and advantages of the present invention will become more readily apparent from the following detailed description when taken in conjunction with the accompanying drawings wherein.

DETAILED DESCRIPTION OF THE PREFERRED EMBODIMENTS

Figure 1:
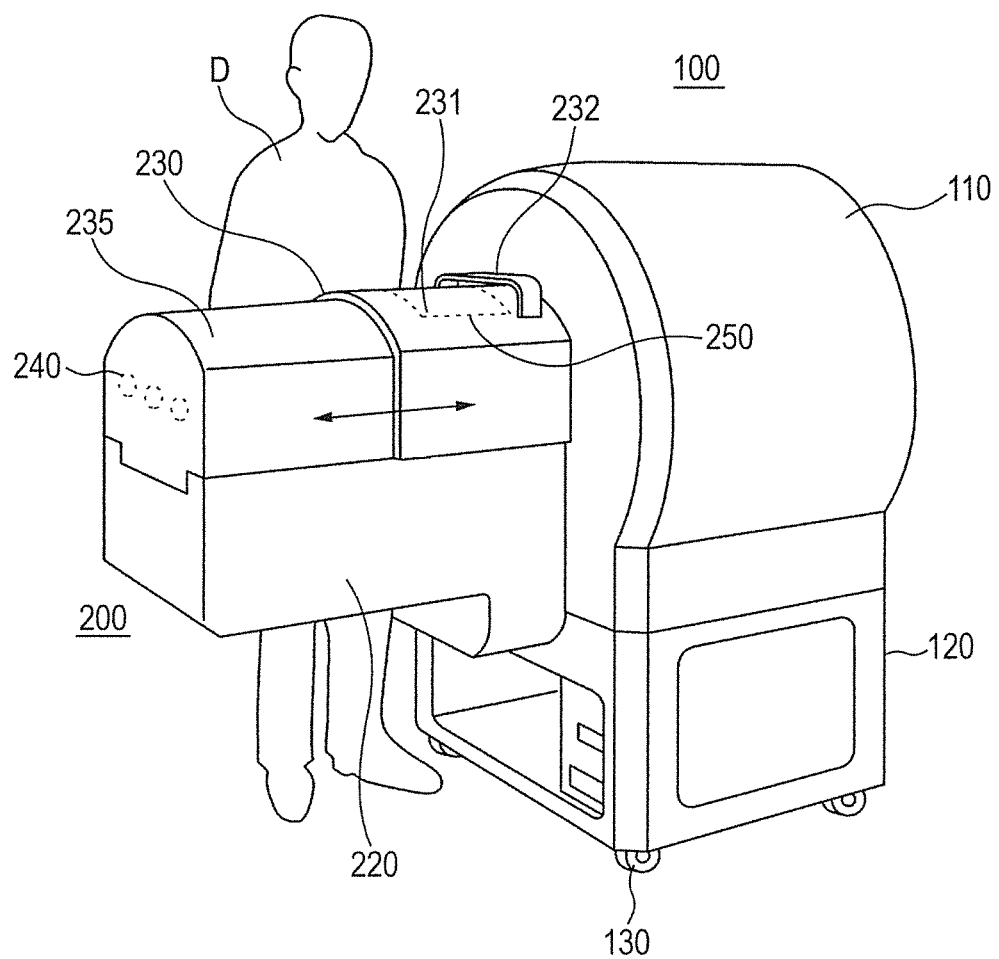
FIG. 1 is a perspective view for showing the outer configuration of an X-ray CT apparatus, according to an embodiment of the present invention.

Hereinafter, explanation will be given fully about an X-ray CT apparatus, according to an embodiment of the present invention, by referring to the drawings attached herewith. However, as a small or middle-sized animal, to be a sample of inspection by using the X-ray CT apparatus, may be considered, for example, a small-size dog, a cat, a rabbit, an exotic animal, etc.; however, in the explanation given hereinafter, a dog will be mentioned, representatively, as an example thereof, and further it will be called, simply, "a sample".

First of all, FIG. 1 attached herewith shows an outlook of an entire of the X-ray CT apparatus, for use of the small and middle-sized animals, according to an embodiment of the present invention. As is apparent from this figure, the X-ray CT apparatus according to the present invention has an outer configuration of being approximately cylindrical, and in an inside thereof, as well as, a gantry portion 110, approximately cylindrical in the outer configuration, for receiving the components therein, including an X-ray irradiating portion therein, which will be mentioned later in details thereof, it has a main body (i.e., a housing) portion 100, built up with a box-like base or pedestrian portion 120, which is attached on a lower portion thereof. Thus, this main body portion 100 has a configuration of deforming a lower portion of a circle to be rectangular (i.e., a tumulus configuration), in the cross-section thereof.

Further, the gantry portion 110 of the main body portion 100 is constructed with, for example, a metal plate, such as, of iron (Fe), etc., or a fiber reinforced resin (FRP), etc., being formed into a desired shape. And, on a lower surface of the pedestrian portion 120, which is formed in a lower portion of this gantry portion 110, is attached a movement means, for moving that apparatus, with ease, i.e., casters 130.

Figure 2:
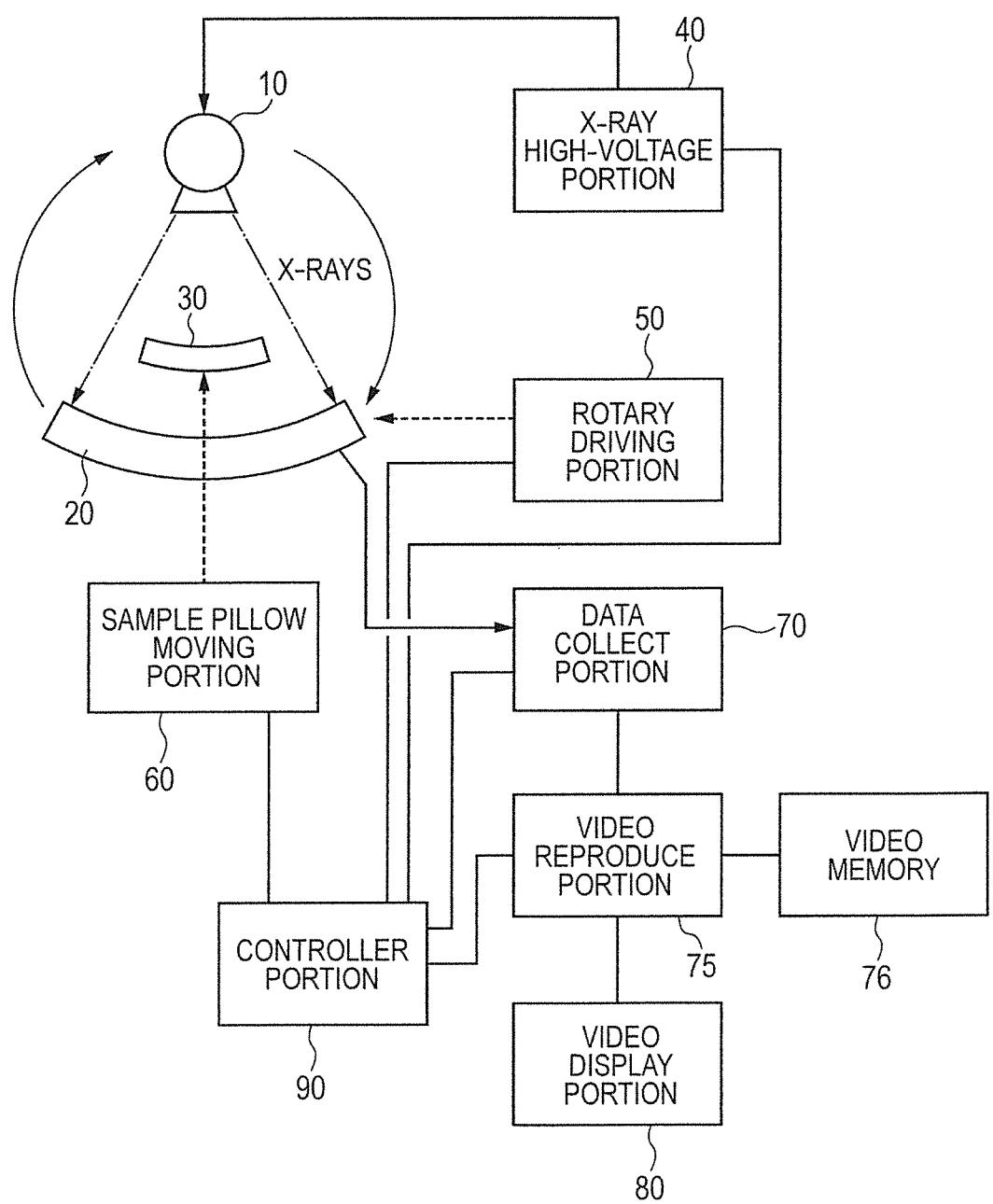
FIG. 2 is a block diagram for showing an example of the interior configuration of the X-ray CT apparatus mentioned above.

Following to the above, in an inside of the housing of the main body portion 100 are provided the components, as is shown in FIG. 2, for building up the X-ray CT apparatus. As an example thereof, as is shown in the figure, in an inside of the gantry portion 110 are provided an X-ray generating apparatus 10 for irradiating X-rays towards to the sample, and an X-ray detecting apparatus 20 for detecting the X-rays, irradiating from that apparatus and passing through the sample, being attached on a ring-like frame not illustrated herein, for example.

Also, in the inside of the housing may be constructed the structure of disposing, not only the components, such as, a sector-like X-rays and an arc-like X-ray detector mentioned above, but also, as is shown in FIG. 3B, applying an X-ray generating apparatus extending in a corn-like manner and a 2-dimensional (2D) detector, for detecting the X-rays irradiating from the X-ray generating apparatus and passing through the sample, and thereby disposing the X-ray generating apparatus and the 2D detector on an arc-like frame. However, the configuration of those should not be limited only to such example as mentioned above.

On the other hand, in a space defined between the X-ray generating apparatus 10 and the X-ray detecting apparatus 20, although the details thereof will be explained later, there is provided a top plate 30, as a table for mounting (or, setting) the sample on an upper surface thereof. Further, a member, in part of which the X-ray generating apparatus 10 and the X-ray detecting apparatus 20 are attached (the details thereof will be explained, hereinafter), is rotated at a predetermined rotating speed in a predetermined direction (please refer to an arrow shown in the figure), by a rotary driving mechanism, such as, a motor, etc., which is provided inside the gantry portion mentioned above. On the other hand, the top plate 30 for mounding the sample thereon is disposed within a space positioning around a central portion of rotating surfaces of the X-ray generating apparatus 10 and the X-ray detecting apparatus 20 mentioned above.

And, in the gantry portion 110 is further provided an X-ray high-voltage portion 40 for supplying high-voltage to the X-ray generating apparatus 10 mentioned above, and a rotary driving portion 50 for rotationally driving a member, attaching the X-ray generating apparatus 10 and the X-ray detecting apparatus 20 thereon, through a rotation control of the motor.

On the other hand, a detection signal from the X-ray detecting apparatus 20 is inputted into a data collect portion 70, to be collected as video data therein, and further, in a video reproduce portion 75, it is reproduced in the form of a cross-section image or a 3D image of an inside of the sample. Further, a reference numeral 76 in the figure a memory device (i.e., a video memory) to be used when the cross-section image or the 3D image of the inside of the sample is reproduced in the video reproduce portion 75. Also, the cross-section image or the 3D image of the inside of the sample, which is reproduced by that video reproduce portion 75, is displayed on a video display portion 80, which is constructed with a liquid crystal display device, etc., for example. Further, if installing so-called a touch panel (not shown in the figure) in this video display portion 80, it is possible to conduct inputting necessary for the operation of the apparatus, through that video display portion 80. However, the present invention should not be restricted to this, but that apparatus may have a keyboard and/or a mouse, etc. (not shown in the figure), in the place of that touch panel.

And, a reference numeral 90 in the figure depicts a controller portion for controlling the operation of each of the parts building up the X-ray CT apparatus mentioned above. In more details thereof, for example, it is constructed with a central processor unit (CPU), a memory device (i.e., a memory), such as, RAM and/or ROM, etc., and further an external memory device, such as, a HDD, etc., and executes necessary controls upon basis of a software or a firmware, for controlling the operation of each portion, which is stored within the memory device.

Figure 3A:
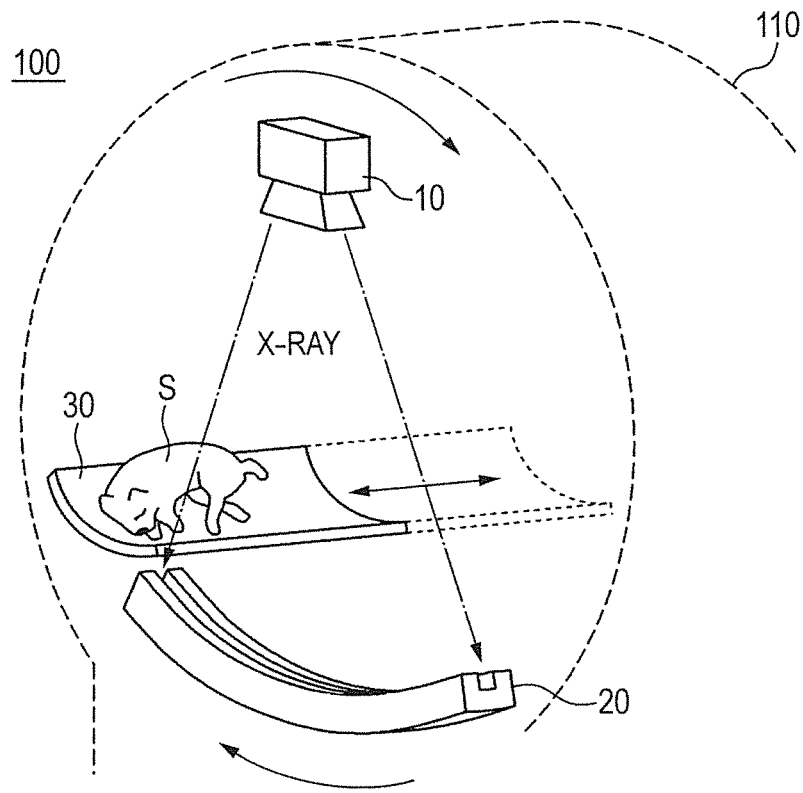
FIGS. 3A and 3B are views for explaining operations for inspecting a cress-section image within the X-ray CT apparatus mentioned above.
Figure 3B:
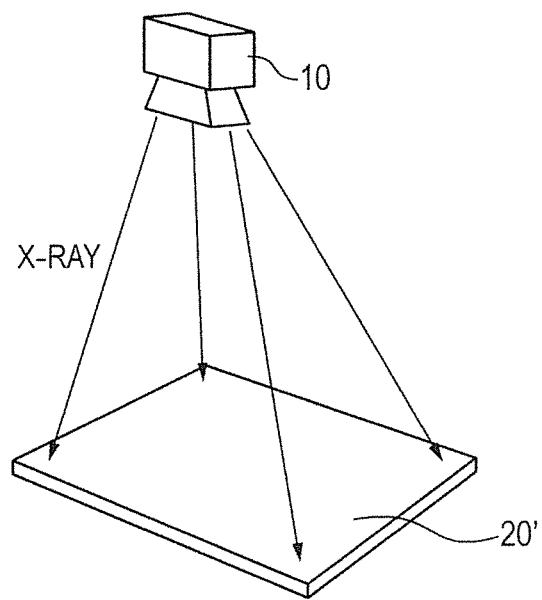

Further, explanation will be given on a detection operation of the cross-section image or the 3D image of the inside of the sample, in the X-ray CT apparatus according to the present invention, the detailed structure of which is given in the above, by further referring to FIGS. 3A and 3B. Thus, with such structure as shown in FIG. 3A, it is possible to obtain video data, with irradiating the X-rays, spirally, on the sample of the top plate 30 (i.e., a helical scanning), through moving the top plate 30, i.e., being a pillow for mounting the sample thereon while rotating the X-ray generating apparatus 10 and the X-ray detecting apparatus 20, as is shown by arrows in the figure. Also, with such structure as shown in FIG. 3B, it is possible to obtain the video data, by irradiating the X-ray in the form of a corn beam, from the X-ray generating apparatus 10, and detecting the X-rays passing through the sample S on a 2D detector 20'. And, reproduction of the video data obtained with this, within the video reproduce portion 75, enables to obtain so-called the cross-section image or the 3D image of the inside of the sample.

Herein, detailed explanation will be given on the member, being attached the X-ray generating apparatus 10 and the X-ray detecting apparatus 20 in a part thereof, and rotating at the predetermined rotation speed into the predetermined direction through the rotary driving mechanism, such as, the motor, etc., by referring to FIGS. 4 and 5.

<Gantry Portion>

Figure 4:
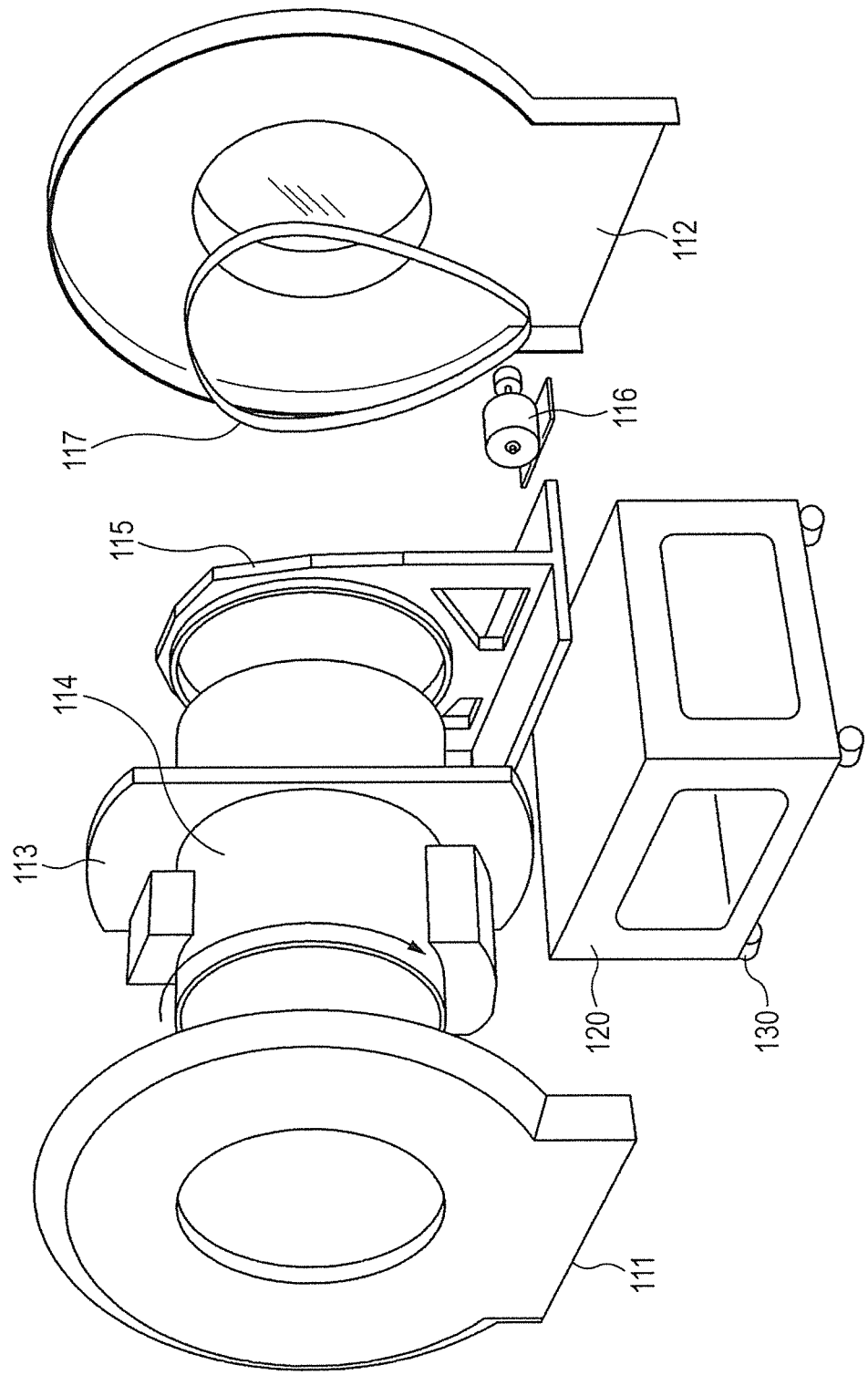
FIG. 4 is an exploded perspective view for explaining the detailed interior structure of a gantry portion of the X-ray CT apparatus mentioned above.

First of all, FIG. 4 is an exploded perspective view of the above-mentioned gantry portion 110. In this figure, in the gantry portion 110 to be mounted on the upper surface of the pedestrian portion 120 mentioned above are provided the following members, at least, in an inside of a space defined by almost disc-like front/rear covers 111 and 112, and an almost semi-cylindrical cover, to be attached so as to cover that pair of covers and also an outer periphery thereof, though not shown in the figure herein. Thus, there are provided a cylinder-like or box-like member 114 (i.e., forming the gantry), one end (e.g., the left end in the figure) thereof being opened (i.e., closed at the right end in the figure) and further being attached with a flange-like member 113 for smoothing the rotation at around a central portion thereof, a frame member 115, being almost ring-like in the outer configuration thereof, for supporting that cylinder-like or box-like member rotatable, and a motor 116 for rotationally drive that cylinder-like or box-like member. Further, as is apparent from the figure, the frame member 115 and the motor 116 are attached on the upper surface of the pedestrian portion 120 mentioned above, fixedly, and a belt 117 is hanged between a pulley attached on an output rotating shaft of the motor 116 and an outer periphery surface of the cylinder-like member 114, whereby so-called rotation of the gantry is conducted (see an arrow in the figure). However, as a shape of the cylinder-like or box-like member mentioned above, i.e., so-called an X-ray shielding member 114 can be considered various one, such as, an oval, an oblong or a hexagon, etc., other than that, and may be in any one of the shapes; however, in the explanation given below, it will be described as the cylinder-like member, representatively.

The X-ray shielding member 114 mentioned above is formed from, for example, a metal plate(s) of iron (Fe), etc., or of fiber reinforced resin (FRP), etc., being formed into a desired configuration, and further on an internal circumferential thereof is backed by lead plates (not shown in the figure herein), for preventing the X-rays from leaking outside. A material for conducting the backing of the X-ray shielding member 114 should not be restricted to this, and it may be a heavy metal (indicating a metal having a specific gravity of 4-5 and greater than that) having a property of shielding the X-rays, for example, or an alloy including the heavy metal therein. In particular, it may be formed of a lead or a lead alloy itself. And, as is shown in FIG. 5, in part of wall surfaces of this X-ray shielding member 114 are formed attachment openings 1141 and 1142, facing to each other with putting the rotary shaft therebetween (see the one-dotted chain line A in the figure), i.e., a rotary center of that cylinder-like member, and on those attachment openings are attached the X-ray generating apparatus 10 and the X-ray detecting apparatus 20 or 20', respectively, as is shown by arrows in the figure. Further, on outer frames of those X-ray generating apparatus 10 and the X-ray detecting apparatus 20 is also treated the backing of the lead plates (not shown in the figure, herein), etc., for preventing the X-rays from leaking outside.

In more details thereof, the lead for backing the X-ray shielding member, being formed to be thin plate-like, having thickness of 2.5 mm is applied in the present embodiment, however an amount thereof applied is 0.002 cubic meter. Since the specific gravity of the lead is 11.34, then converting it into the weight, it can be said that the lead of 23 kg is sufficient, in particular, for the X-ray shielding member 114 of the apparatus according to the present invention. However, for the purpose of comparison, when backing the apparatus as a whole thereof (i.e., an entire housing of apparatus outside) by the lead, there is necessity of an amount of lead exceeding 500 kg; however, comparing to this, according to the present invention, it is possible to decrease the amount of lead, greatly, and thereby to achieve light-weighting of the apparatus.

The X-ray shielding member 114 mentioned above is made by forming the metal plate of iron (Fe), etc., or the fiber reinforced resin (FRP), etc., into a desired shape, and further, for preventing the X-rays from leaking outside, it may have the structure, not only backing the inner peripheral surface thereof with the lead plate(s) (herein, not shown in the figure), but also being formed from a heavy metal, a material including heavy metal, or an alloy including heavy metal therein, i.e., having an X-ray shielding effect by itself. In this case, it brings about no cost for backing, nor ablation of the backing material due to the lapse of time.

Thus, with such structure of the gantry including the cylinder-like member 114 as mentioned above, the X-rays irradiating from the X-ray generating apparatus 10, basically, pass through an interior space through an opening portion 1141 of the cylinder-like member 114, and after passing through the interior space, reach to the X-ray detecting apparatus 20. However, apart of that X-rays, though trying to leak outside from the opening an end of the cylinder-like member 114, but in the present embodiment, it is shielded by a sample setting portion 200, which will be mentioned in the derails thereof hereinafter, and in more details, it does not leak outside the structure of the gantry including the sample setting portion 200 therein.

However, in the explanation given in the above, with the structure of the gantry including the cylinder-like member 114 mentioned above therein, though the explanation is made that the X-ray generating apparatus 10 and the X-ray detecting apparatus 20 are attached in part thereof; however the present invention should not be restricted to this, for example, other than that, it may be constructed in one (1) body, including the X-ray high-voltage portion 40, for generating and supplying the high-voltage to the above-mentioned X-ray generating apparatus 10, etc. However, in that instance, it may be attached with using the flange-like member 113 mentioned above. Also, as a molding material for preventing from discharging at a high-voltage generating portion in the X-ray generating apparatus 10, it is preferable to adopt a material having a large specific gravity, being high in the X-ray shielding effect, and further having an insulating effect, such as, bismuth, etc., and as such molding material can be applied for preventing the X-rays from leaking outside, in other parts than that.

And, with such structure of the gantry portion 110 as mentioned above, as an example thereof, by determining the diameter of the cylinder-like member 114 mentioned above, i.e., a bore size, to be 360 mm, for example, it is possible to achieve a CT photographing FOV (Field of View=diameter of a region of photographing of CT) of 240 mm; i.e., enabling the photographing of, not only a small-size dog, but also a middle-size dog, further.

<Sample Setting Portion>

Next, explanation will be given on the details of the sample setting portion 200 mentioned above, by referring to FIGS. 6A and 6B, in addition to FIG. 1 mentioned above.

In FIG. 1 is shown the sample setting portion 200 in the condition of being closed, and as is apparent from the figure, that sample setting portion comprises a lower cover portion 220, being formed in an approximately "L"-like shape for building up a lower portion thereof, and a cover portion 230, being attached on an upper surface of that lower cover portion 220 and semi-cylindrical in the outer shape (being an approximately "U"-like in the cross-section), and in particular, that cover portion 230 has the structure of being able to open. Further, this sample setting portion 200 is formed in a desired configuration from the fiber reinforced resin (FRP), etc., similar to such main body (i.e., the gantry) portion as mentioned above, including that lower cover portion 220 and the cover portion 230, being attached on an upper surface of that lower cover portion 220 and semi-cylindrical in the outer shape (being an approximately "U"-like in the cross-section), and also being backed by the lead plate(s) (not shown in the figure herein) on the interior surface thereof.

Furthermore, this cover portion 230, as apparent from FIG. 1, has such a structure that it can open into two (2) stages. Thus, it is constructed with an outer cover portion 231 and an inner cover portion 235. Those outer cover portion 231 and inner cover portion 235 are attached so that they can slide with respect to the lower cover portion 220 mentioned above, and as a sliding member for that, for example, a rail(s), a roller(s) and/or a slider(s), etc., can be also attached with. Also, the cover portion 230, in particular, on an upper portion of the outer cover 231 is attached a grip 232 for moving that cover portion 230 in the horizontal direction (slide: please refer to an arrow in the figure).

Figure 6A:
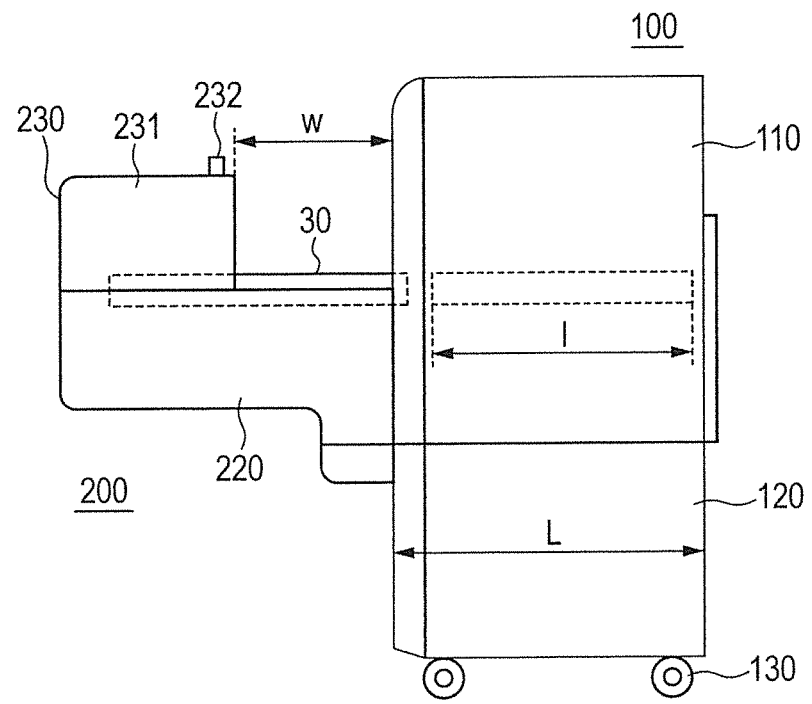
FIGS. 6A and 6B are side surface views for explaining the detailed structures of a sample setting portion and a cover portion thereof, within the X-ray CT apparatus mentioned above.

And, as is shown in FIG. 6A, the length "L" of the main body portion 100 in the horizontal direction is determined to be nearly equal to the length "l" of the top plate 30, i.e., the sample mounting table that moves between the main body portion 100 while mounting the sample thereon, or less than that. With this, it is possible to reduce the X-ray CT apparatus, in particular, the largeness (i.e., the sizes) of the main body portion 100 thereof, greatly. Thus, accompanying with the great reduction of the sizes of the main body portion 100 (i.e., small-sizing), it is possible to reduce an amount of use of the members, each being backed by the lead plate(s) on the interior surface thereof and relatively expensive and large in the weight thereof, and thereby enabling reduction of the manufacturing costs and the weight of the apparatus. However, in FIG. 6A or 6B, the top plate 30 moving between the main body portion 100 is shown by a thick solid line, when it is in the condition when it projects outside from that main body portion at the most, while by a broken line in the condition when it moves into a position deepest within that main body portion, respectively.

Also, with the sample setting portion 200 (including the cover portion 230 and the lower cover portion 220 in the lower portion thereof), extending towards outside from an about central portion of the main body portion 100 and being attached in a sleeve-like manner, similarly, the length thereof in the horizontal direction (i.e., the depth) may be determined to be nearly equal to the length "l" of the top plate 30, i.e., being the sample mounting table, or less than that, and with this, it is possible to reduce the largeness (i.e., the sizes) thereof, greatly, comparing to the conventional structure of covering the X-ray CT apparatus with using the members, being backed by the lead plate as a whole thereof.

And, with such sample setting portion 200 as mentioned above, in particular, as is apparent from FIG. 1 mentioned above, because of the configuration thereof, an operator "V" of the apparatus (for example, a veterinarian) can set the sample on the top plate 30, easily, by opening/closing the cover portion 230 (in more details, by moving the grip 232 of the cover portion 230, horizontally), under the condition of standing at the position neighboring with the sample setting portion 200 (i.e., beside it). Namely, comparing to opening a door, which is provided on one (1) surface of the apparatus, thereby setting the sample on the top plate 30 inside through that door, as conventional, it is superior in the operability. Further, in FIG. 4A is shown the condition when moving only the outer cover 231 so as to open the cover portion 230 (i.e., opening the cover portion only to a first stage), and width "w" of the opening, which can be obtained in this condition, is set to 370 mm, as an example thereof. Also, with provision of the sample setting portion 200 at around the central portion of the apparatus, in more details thereof, at around the central portion on one (1) surface of the side surfaces, on both ends of the main body (housing) portion 100 having the almost cylinder-like configuration, in a rotational axis direction thereof, it is possible to set the sample on the top plate 30 from both sides of that sample setting portion, for plural numbers of operators "V", and this is preferable because of increasing the convenience thereof.

Figure 6B:
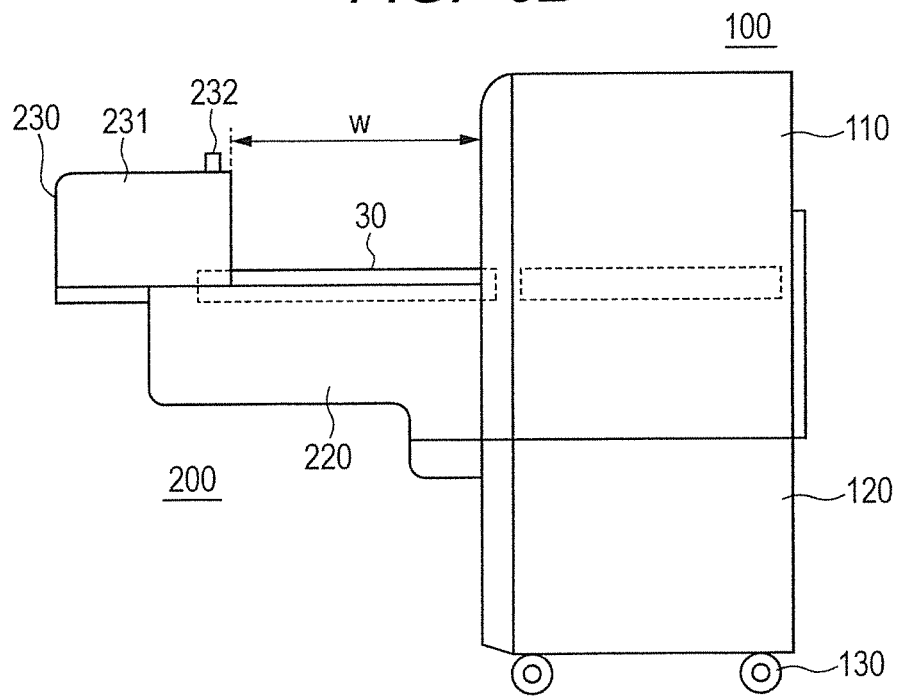

In FIG. 6B is shown the condition of moving also the inner cover portion 235 together with (in one body) the outer cover portion 231, building up the cover portion 230, to an outside (i.e., opening it up to the second stage). The width "W" in this instance is determined to be 600 mm, for example. With this, i.e., with the structure of the cover portion 230, being able to open/close at multi-stages, it is possible to deal with, even when a pet, i.e., the sample, is relatively large in the size, easily.

Figure 7:
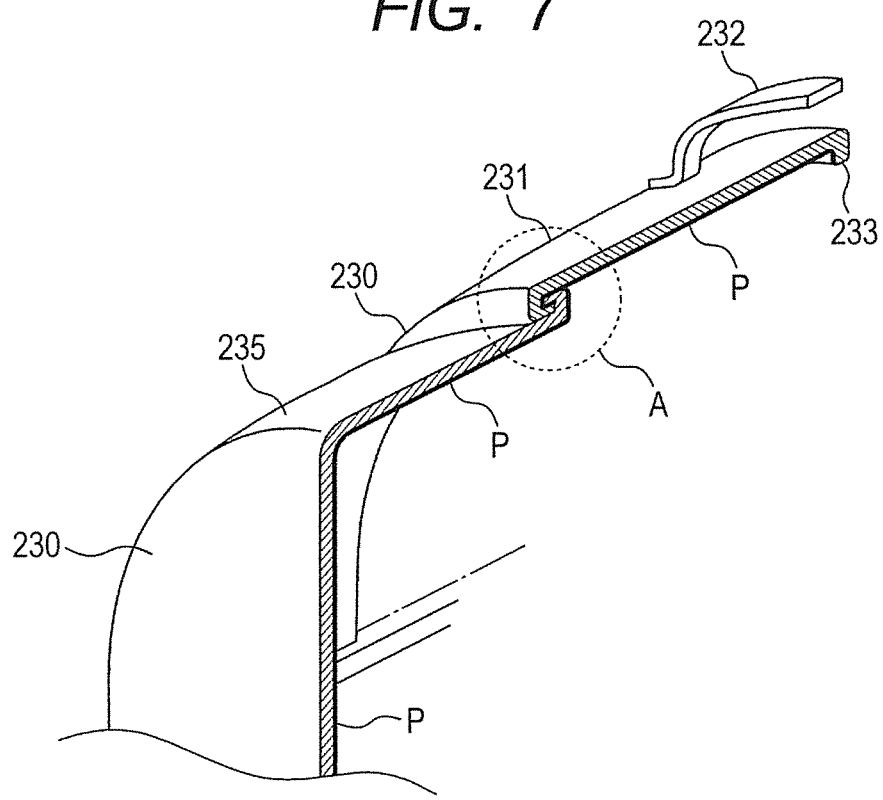
FIG. 7 is a partial enlarged perspective view, including a cross-section thereof in a part, for explaining an example of the structure of the cover portion mentioned above.

In FIG. 7 attached herewith is shown an example of the structure of the cover portion 230 mentioned above, in the form of a perspective view, including a cross-section of part thereof, wherein the lead plates "P" are backed on an entire surface of the interior surfaces of the outer cover portion 231 and the inner cover portion 235, as is indicted by a thick solid lines in this figure. With such structure, no X-ray leaks outside from that cover portion 230, under the condition of being closed, and for that reason, for the operator, it is possible to conduct the operation, with safety, even in the periphery of the X-ray CT apparatus. It is important to adopt the structure of not allowing the X-rays to leak outside from a gap, in particular, the connecting portion between the outer cover portion 231 and the inner cover portion 235 themselves, being the movable portions, the connecting portion between the lower cover portion, and further the connecting portion between the main body portion 100.

Figure 5:
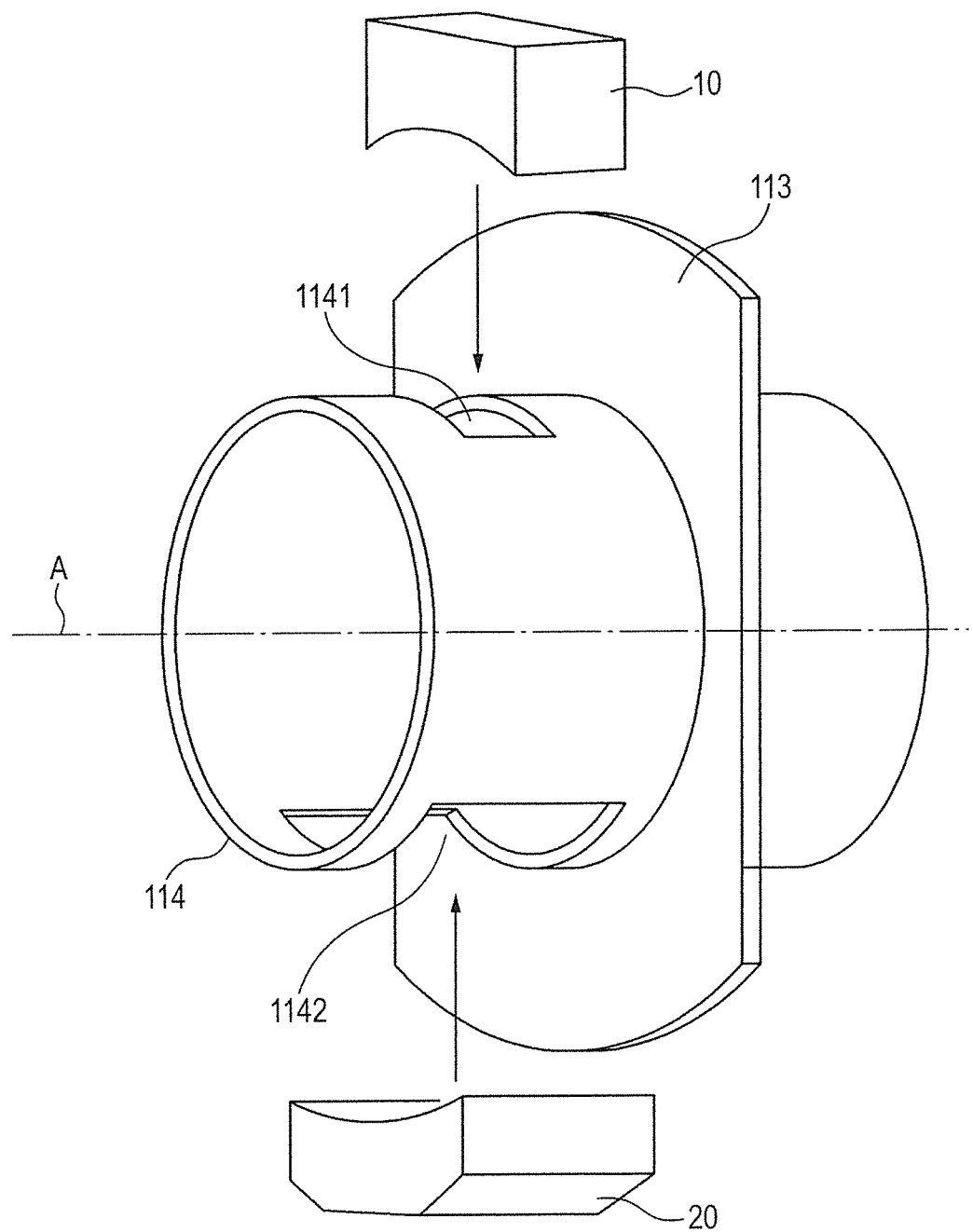
FIG. 5 is an enlarged and exploded partial view for showing the detailed structure of X-ray shielding members for building up the gantry portion mentioned above.

Also, a projection inside (i.e., a flange portion) at one end of the outer cover portion 231, shown by a reference numeral 233 in FIG. 5, is a such structure that it abuts or contacts on an end portion of the inner cover portion 235, during when that outer cover 235 further moves to the second stage, and thereby moving that inner cover portion together with the outer cover portion.

Figure 8A:
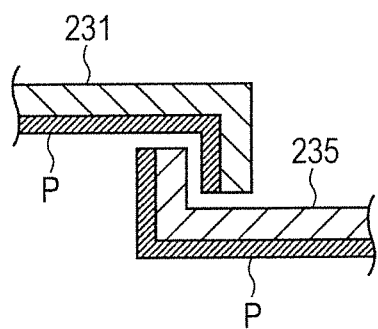
FIGS. 8A and 8B are enlarged cross-section views of a portion "A" shown by broken line in FIG. 5 mentioned above, i.e., the connecting structures at ends thereof, between an external cover portion and an interior cover portion of the cover portion mentioned above.
Figure 8B:
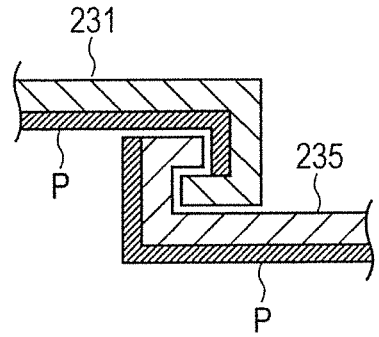

In FIGS. 8A and 8B is shown the connecting structure between the outer cover portion 231 and the inner cover portion 235 mentioned above at end portions thereof, namely, an enlarged cross-section of a portion "A" shown by a broken line in FIG. 5. As is apparent from those figures, the interior surfaces of the outer cover portion 231 and the inner cover portion 235 are backed by the lead plates "P", and further, those lead plates "P" are arranged to cover or pile up with each other, at that connecting portion; i.e., thereby achieving the structure of preventing the leakage of X-rays, with certainty, at that connecting portion.

Figure 9:
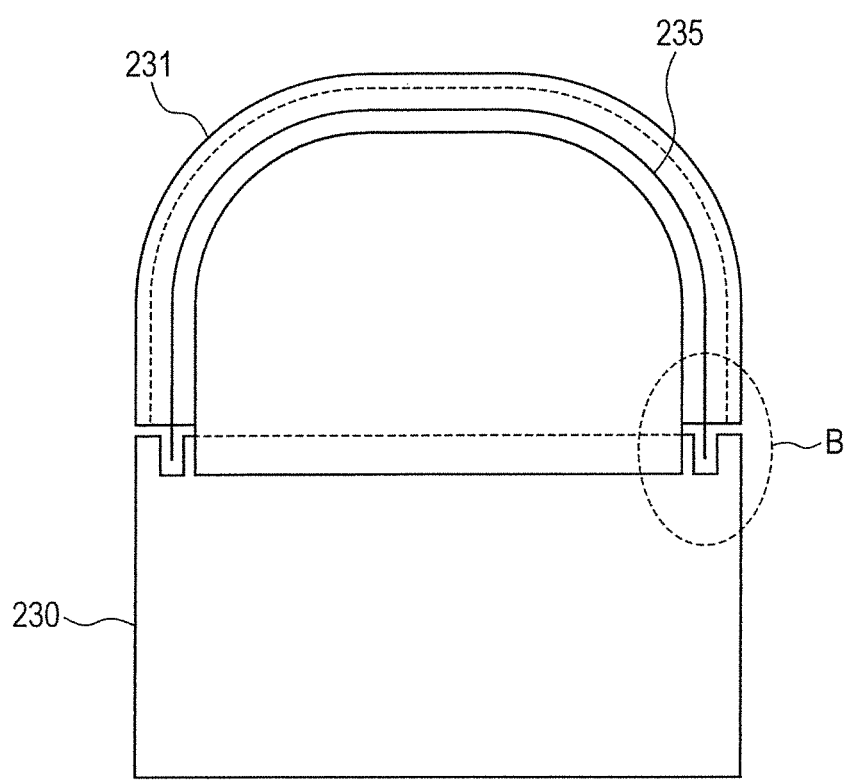
FIG. 9 is a plane view of the external cover portion and the interior cover portion mentioned above.
Figure 10:
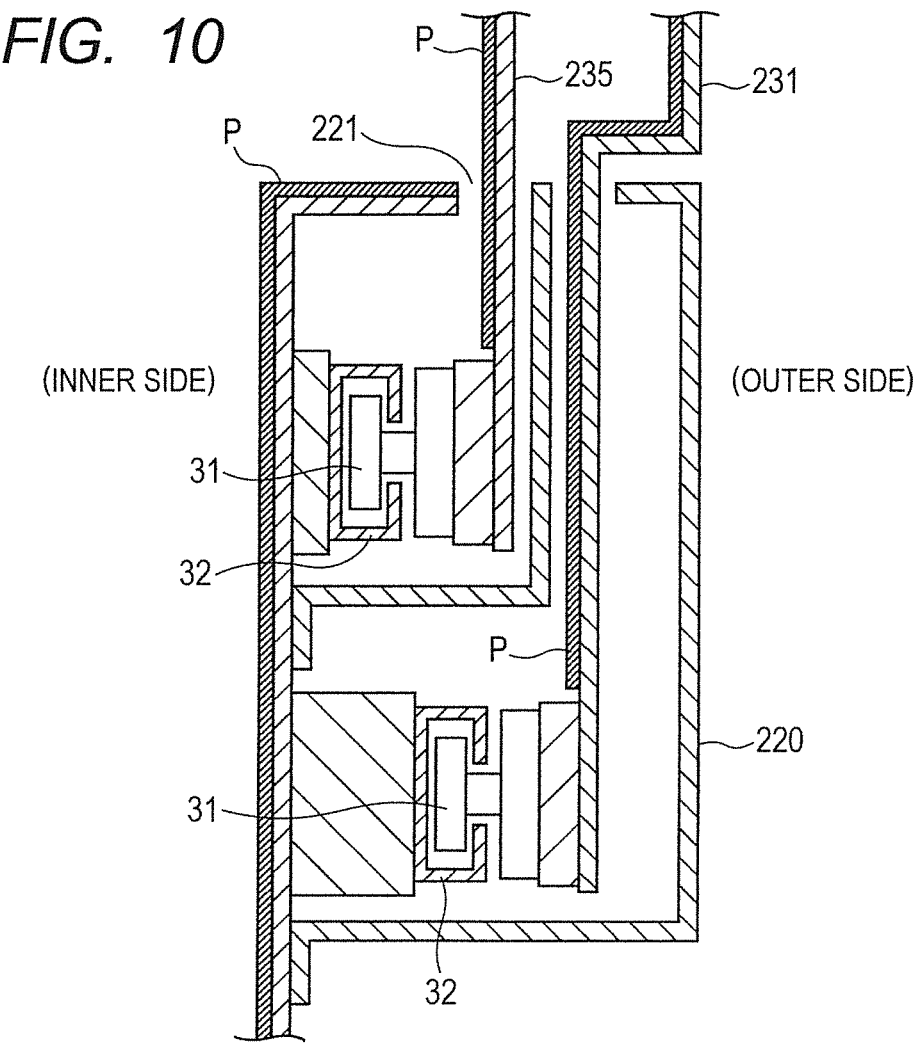
FIG. 10 is an enlarged cross-section view of a portion "B" shown by a broken line in FIG. 7 mentioned above, i.e., a sliding mechanism at ends of the external cover portion and the interior cover portion mentioned above.

Also, FIG. 9 shows a plane view of the outer cover portion 231 and the inner cover portion 235 mentioned above, and further in FIG. 10 is shown an enlarged cross-section of a portion "B" shown by a broken line in that figure. Thus, in those figures, the outer cover portion 231 and the inner cover portion 235 are inserted into an inside of the lower cover portion 220 mentioned above, through an opening portion 221, which is provided on an upper portion thereof, and they are freely movable with respect to the lower cover portion 220, respectively, because of the functions of a guide roller 31, which is attached at a tip portion thereof, and a slide rail 32, which is attached on a side of the lower cover portion 220. And, as is apparent from the figure, the lead plates "P" backed on the interior surfaces of the outer cover portion 231 and the inner cover portion 235 are so arranged to cover or pile up with each other, even in that sliding portion, and thereby achieving the structure of not allowing the X-rays to leak outside from the gap.

In addition thereto, it is also possible to provide a window portion for observing an inside, in a part of the sample setting portion 200 mentioned above, in more details, as is shown by a broken line 250 in FIG. 1 mentioned above, the outer cover portion 231 and/or the inner cover portion 235, building up the cover portion 230 mentioned above. However, in that case, as a transparent body for building up that window portion may be applied, for example, a glass including the leas therein.

Figure 11:
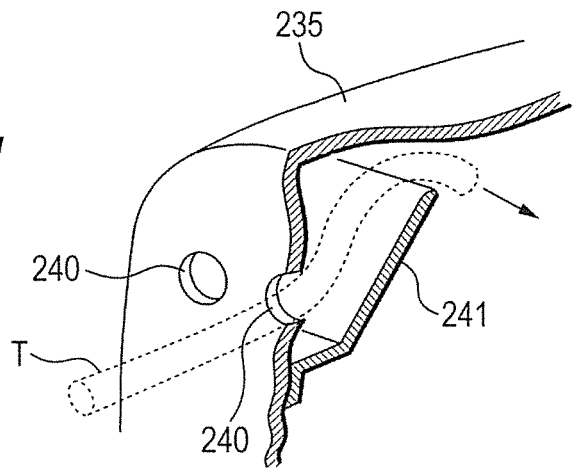
FIG. 11 is an enlarged perspective view, including a cross-section thereof in a part, for showing the detailed structures of an opening for introducing a tube, which is provided in a part of the cover portion mentioned above.

Further, as is shown in FIG. 11 attached herewith, an introduction opening 240 for a tube may be provided in a part of a wall of the inner cover portion 235 (in an example shown in the figure, in a wall at the tip), for introducing a gas or a liquid in an inside through that introduction opening. However, in that instance, as is shown by a reference numeral 241 in the figure, a member backed by the lead plate is attached, covering a periphery of that introduction opening 240 under the condition of keeping such a gap that the tube can pass through, in other words, that introduction opening cannot be seen when seeing it from the inside of the cover portion 230 mentioned above. With such the structure, it is possible to introduce or guide an anesthetic (for example, a gas), etc., for example, to the sample mounted within the inside of the sample setting portion 200, and further to prevent the X-rays from leaking, from that introduction opening 240.

And, by attaching such sample setting portion 200 as was mentioned above on a front surface of the gantry portion (a surface, on which an opening portion 1141 of the cylinder-like member 114 appears; i.e., the left-end surface in FIG. 1), as is shown in FIG. 1 mentioned above, it is possible to obtain an almost box-like X-ray CT apparatus having the sample setting portion 200 for setting the sample therein, being formed in the sleeve-like manner projecting from an approximately central portion (including a portion of the pedestrian portion 120) on one (1) surface of the cylinder-like gantry portion 110 towards outside. Further, it may be preferable to adopt so-called a nesting or telescope structure therein, for example, for preventing the leakage of the X-rays from the gap defined between the gantry portion 110 and the sample setting portion 200.

In this manner, with the X-ray CT apparatus according to the present invention, the X-rays, trying to leak outside from an end of the cylinder-like member 114 building up such gantry portion 110, are shielded by the sample setting portion 200, having such a structure that no X-ray leaks outside by, being formed by the members, on outer peripheral walls thereof being backed by the lead plates, as was mentioned above, and for that reason, no X-ray leaks outside from the apparatus.

And, in such the X-ray CT apparatus according to the present invention, in the similar manner to that in the CT for the human-use, with adopting such a structure that a bed (i.e., the top plate) is prepared to be the sample setting portion, for a pet to sleep thereon, and that the top plate slides into the gantry, smoothly, lightening of a load upon a human being for operating the apparatus is achieved. Thus, no such a job in an over-tasking posture, for example, twisting a body under the condition of holding a relatively heavy pet of 5 kg-10 kg, as was mentioned in the conventional technology in the above, is compelled for a women veterinarian or nurse, who possibly does that job, as well as, for her, it is possible to set the pet, as the sample, therein with an ease, and as a result thereof, it is possible to bring the pet to be quiet within the apparatus, during the time of inspecting, without falling into an anxious condition, and therefore possible to obtain a preferable cross-section image or the 3D image.

However, the sample setting portion 200 may be fixed on the gantry portion 110 in one body, or alternately, when taking the movement and/or transportation of the apparatus into the consideration thereof, may be preferable to be freely detachable depending on the necessity thereof. Further, also in that instance, as was mentioned previously, it is needless to say that there is a necessity of such structure for preventing the leakage of the X-rays from the gaps, which may be defined between the respective portions thereof.

Also, the X-ray CT apparatus according to the present invention should not be restricted to such structure as mentioned above; i.e., forming the sample setting portion 200 and the gantry portion 110 in one (1) body, but in the place of the sample setting portion 200 mentioned above, it may be such structure that a human being inserts the bed (i.e., the top plate) mounting the pet thereon into the gantry portion 110. However, in such case, it is of course for the person skilled in the art, that a means (for example, a cover-like member, which is formed from a member backed by the lead plate, etc.), is necessary, for shielding the X-rays trying to leak outside from the opening portion at an end of the cylinder-like member 114 building up the gantry portion 110.

However, in the above, the explanation was made that the cover portion 230 mentioned above is able to open/close in the two (2) stage manner; but the present invention should not be restricted to this, and for example, it may be in a multi-stage type of three (3) stages or more than that. Also, in the above, the explanation was made that the cover portion 230 is in the structure of being able to open/close by moving (i.e., sliding) a part thereof in the horizontal direction; but the present invention should not be restricted to this, and for example, a rotary door may be provided in a part thereof, to be able to open/close by rotating that door.

And, with the moving mechanism, including the motor for moving such top plate, i.e., the sample mounting table, as mentioned above, it may be preferable to be stored within the lower cover portion 220 locating below the cover portion 230, from a viewpoint of small-sizing of the apparatus.

The present invention may be embodied in other specific forms without departing from the spirit or essential feature or characteristics thereof. The present embodiment(s) is/are therefore to be considered in all respects as illustrative and not restrictive, the scope of the invention being indicated by the appended claims rather than by the forgoing description and range of equivalency of the claims are therefore to be embraces therein.

What is claimed is:

1. An X-ray CT apparatus for obtaining a cross-section image or a 3D image of an inside of a sample with X-rays, comprising:
    an X-ray generating apparatus, which is configured to irradiate the X-rays on the sample;
    an X-ray detecting device, which is configured to detect the X-rays passing through the sample; and
    a device, which is configured to process a detection signal from the X-ray detecting device and obtain the cross-section image or the 3D image of the inside of the sample;
    a gantry including an X-ray shield having an opening portion at one end to introduce the sample therein and treated with an X-ray protection process on an entire periphery thereof;
    a motor to drive rotation of the X-ray shield around a rotational axis; and
    a sample setting portion attached to the gantry around the opening portion of the X-ray shield, wherein:
    the sample setting portion has an outer peripheral wall formed with the X-ray shield, a part movable to open and close, and a to plate to move the sample into an inside of the X-ray shield,
    the X-ray generating apparatus and the X-ray detecting device are respectively treated with the X-ray protection process, are fixed on a wall surface of the X-ray shield at positions opposing each other with the rotational axis therebetween, and constructed with the X-ray shield in one body.

2. The X-ray CT apparatus according to claim 1, wherein the X-ray shield is treated with the X-ray protection process by backing a thin plate of a heavy metal or a heavy metal alloy thereon.

3. The X-ray CT apparatus according to claim 1, wherein the X-ray shield is made of a plate of a heavy metal or a heavy metal alloy as the X-ray protection process.

4. The X-ray CT apparatus according to claim 1, wherein an observation window is disposed in a part of the outer peripheral wall formed with the X-ray shield for forming the sample setting portion.

5. The X-ray CT apparatus according to claim 2, wherein an observation window is disposed in a part of the outer peripheral wall formed with the X-ray shield for forming the sample setting portion.

6. The X-ray CT apparatus according to claim 3, wherein an observation window is disposed in a part of the outer peripheral wall formed with the X-ray shield for forming the sample setting portion.

7. The X-ray CT apparatus according to claim 1, wherein an introduction opening is disposed in a part of the outer peripheral wall formed with the X-ray shield for forming the sample setting portion, and the outer peripheral wall includes a plate to prevent leakage of the X-rays from the introduction opening.

8. The X-ray CT apparatus according to claim 2, wherein an introduction opening is disposed in a part of the outer peripheral wall formed with the X-ray shield for forming the sample setting portion, and the outer peripheral wall includes a plate to prevent leakage of the X-rays from the introduction opening.

9. The X-ray CT apparatus according to claim 3, wherein an introduction opening is disposed in a part of the outer peripheral wall formed with the X-ray shield for forming the sample setting portion, and the outer peripheral wall includes a plate to prevent leakage of the X-rays from the introduction opening.

10. An X-ray CT apparatus, comprising:
an X-ray generating apparatus to irradiate X-rays on a sample;
an X-ray detecting device to detect the X-rays passing through the sample; and
a controller which receives a detection signal from the X-ray detecting device and produces a cross-section image or a 3D image of an inside of the sample;
a gantry including an X-ray shield having an opening at one end to introduce the sample therein;
a motor to drive the X-ray shield to rotate around a rotational axis; and
a sample setting portion attached to the gantry around the opening of the X-ray shield, wherein:
the sample setting portion has an outer peripheral wall formed with an X-ray shield, a part thereof being constructed to be able to open/close, and a top plate for moving the sample into an inside of the X-ray shield, and
the X-ray shield includes metal plating on an entire periphery thereof;
the X-ray generating apparatus and the X-ray detecting device include metal plating on a periphery thereof, are fixed on a wall surface of the X-ray shield at positions opposing each other with the rotational axis therebetween, and constructed with the X-ray shield in one body.

11. The X-ray CT apparatus according to claim 10, further comprising:
an observation window disposed in the outer peripheral wall of the sample setting portion.

12. The X-ray CT apparatus according to claim 10, further comprising:
an introduction opening disposed in the outer peripheral wall of the sample setting portion, and the outer peripheral wall includes a plate to prevent leakage of the X-rays from the introduction opening.

13. The X-ray CT apparatus according to claim 11, further comprising:
an introduction opening disposed in the outer peripheral wall of the sample setting portion, and the outer peripheral wall includes a plate to prevent leakage of the X-rays from the introduction opening.

* * * * *